United States Patent [19]

Deckers et al.

[11] Patent Number: 5,380,892

[45] Date of Patent: Jan. 10, 1995

[54] PROCESS FOR SEPARATING ALIPHATIC STRAIGHT-CHAIN COMPOUNDS HAVING TERMINAL FUNCTIONAL GROUPS FROM ALPHA-ISOMERS THEREOF

[75] Inventors: Gregor Deckers, Xanten; Dieter Frohning, Wesel, both of Germany

[73] Assignee: Hoechst Aktiengesellschaft, Germany

[21] Appl. No.: 909,365

[22] Filed: Jul. 6, 1992

[30] Foreign Application Priority Data

Jul. 12, 1991 [DE] Germany .............................. 4123084

[51] Int. Cl.⁶ ................................................ C11C 1/08
[52] U.S. Cl. ...................................... 554/186; 564/1.5; 568/699; 568/923
[58] Field of Search ...................... 554/186; 564/1.5; 568/699, 923

[56] References Cited

FOREIGN PATENT DOCUMENTS 415697 3/1991 European Pat. Off. ... C07C 53/126

OTHER PUBLICATIONS

Chemical Abstracts, vol. 80, No. 9, Mar. 4, 1974 Abstract#474 17h.
Industrial & Engineering Chemistry, vol. 42, pp. 1300–1306 Jul. 7, 1950.

*Primary Examiner*—José G. Dees
*Assistant Examiner*—Samuel Barts
*Attorney, Agent, or Firm*—Jordan B. Bierman

[57] ABSTRACT

A process for separation of aliphatic straight-chain compounds having terminal functional groups from mixtures containing isomers thereof branched in the α-position by precipitating the aliphatic, straight-chain compounds as their clathrates.

25 Claims, No Drawings

PROCESS FOR SEPARATING ALIPHATIC STRAIGHT-CHAIN COMPOUNDS HAVING TERMINAL FUNCTIONAL GROUPS FROM ALPHA-ISOMERS THEREOF

This Application claims the priority of German Application P 41 23 084.1, filed Jul. 12, 1991.

The present invention relates to a process for separating aliphatic straight-chain compounds having terminal functional groups from mixtures containing their isomers.

BACKGROUND OF THE INVENTION

Because the boiling points of isomeric compounds are very close to each other, customary methods, such as distillation, often prove to be unsuitable for separation thereof. Distillation columns having a large number of trays are necessary because of these small boiling point differences. For sharp separations, the distillation should be carried out at a high reflux ratio, which leads to long residence times in the columns and, therefore, to a considerable exposure to heat of the material to be distilled. Exposure to heat usually results in a reduction in yield, and is particularly adverse in the case of sensitive compounds. Such compounds are discolored in a manner such that they cannot be decolorized by distillation; moreover, undesirable by-products are formed. Needless to say, distillation can be used as a separation method only on distillable substances. In contrast, substances which suffer degradation or thermal decomposition as a result of distillation are unsuitable for separation by this method.

Fractional crystallization, likewise a customary separation method, can also be used to only a limited extent. On the one hand, this process is limited to crystallizable substances and, on the other hand, fractional crystallization is highly labor-intensive. Moreover, it entails substantial expenditures on apparatus, in particular because of the numerous individual crystallization steps usually required.

The isolation and purification of methyl-branched saturated fatty acids having 14 to 24 carbon atoms by means of a particular variant of fractional crystallization is described in DE 38 07 401 A1. An aqueous solution of a wetting agent is added to the molten fatty acid mixture, and the mixture is allowed to crystallize while being stirred. This process is called hydrophilization, or fractional crystallization in the presence of wetting agents. The dispersion obtained by this process is centrifuged, separated into a lighter phase, containing the methyl-branched fatty acid largely free of wetting agent, and a heavier phase, consisting of wetting agent solution and crystals of straight-chain saturated fatty acids dispersed therein.

Specific methods for separation and concentration of aliphatic compounds are also used to a limited extent. Zimmerschied, Dinerstein, Weitkamp and Marschner thus describe, in Ind. Eng. Chem. 1950, 42 (7), pages 1300 to 1306, crystalline adducts of urea with linear aliphatic compounds. The formation of urea inclusion compounds depends on various factors, including the chain length and linearity of the aliphatic compound. However, the nature and size of the substituents, and the number and position thereof, also have an influence on the formation of the urea inclusion compounds. If the chain length is adequate, slightly branched alkanes also lead to urea adducts. Thus, for example, 2-methyloctadecane forms a urea inclusion compound, the stability of which is comparable to that of n-hexadecane. Similar behavior is also exhibited by esters of fatty acids; esters of methyl-branched carboxylic acids also form urea inclusion compounds (cf. page 1302, left-hand column to page 1303, left-hand column, second paragraph).

British Patent 1,240,513 describes the production of a therapeutically usable mixture consisting of esters of linoleic acid and $\gamma$-linolenic acid. By addition of urea to a solution of esters of palmitic, stearic, oleic, linoleic, and $\gamma$-linolenic acid in methanol, a mixture which is predominantly esters of palmitic, stearic, and oleic acid is precipitated as urea inclusion compounds thereof. The desired therapeutically usable mixture of esters of linoleic and $\gamma$-linolenic acid is obtained by subsequently extracting the solution which remains with a suitable organic solvent. However, this procedure is limited to the separation of esters of non-branched saturated and unsaturated carboxylic acids.

SUMMARY OF THE INVENTION

The object of the present invention is to provide a process which avoids the disadvantages described above and, at the same time, can be carried out with relatively little effort. Moreover, the process should ensure good separation of the desired compounds.

This object is achieved by a process for separating aliphatic, straight-chain compounds having terminal functional groups from mixtures containing isomers branched in the $\alpha$-position. The process comprises the addition of a solvent and urea to the mixture, if appropriate heating the mixture, allowing a urea inclusion compound (clathrate) formed to crystallize out by subsequent cooling, and liberating the aliphatic compound from the clathrate which has crystallized.

DETAILED DESCRIPTION OF THE INVENTION

In contrast to pure urea, which forms tetragonal prisms, urea clathrates crystallize in a hexagonal lattice which has long connected channels. The molecules of foreign substances (guest molecules) are incorporated in these channels. The urea molecules build up six-sided prisms having a cross section similar to a honeycomb.

Because of highly pronounced van der Waals forces between urea and the guest molecule, the guest molecules stabilize the hexagonal lattice of the clathrate. The molecules of the foreign substance are consequently not always included in a particular spatial arrangement. Long chain hydrocarbons and derivatives thereof are usually incorporated with their longitudinal axes in the axes of the six-sided prisms.

The hexagonal lattice, viewed by itself, is not stable and collapses as soon as the molecules incorporated are removed by evaporation or extraction. Thus, aliphatic compound as the guest molecule can be readily liberated from the crystallized urea clathrate in this manner. The aliphatic compound to be separated should have an unbranched chain of adequate length. The chain should accordingly comprise at least 8 carbon atoms. Aliphatic straight-chain compounds having 8 to 24, in particular 8 to 22, preferably 10 to 19, carbon atoms in the non-branched chain are particularly suitable.

The process according to the invention can be used for separating aliphatic, straight-chain compounds which contain, as a terminal functional group on one or both ends of the carbon chain, an alcohol, amine, ether, carboxylic acid, or carboxylic acid ester radical. Particularly useful are amines, carboxylic acids, or carboxylic acid ester radicals, most preferably carboxylic acid radicals.

Alcohols worthy of special mention are n-octanol, n-undecanol, n-hexadecanol, n-octadecanol, and n-nonadecanol, in particular, n-undecanol and n-nonadecanol. Examples of amines are 1,8-diaminooctane and 1,12-di-aminododecane, and examples of ethers are n-alkyl tert-butyl ethers, in which n-alkyl represents a group having 8 to 24 carbon atoms.

Suitable carboxylic acids are undecanoic, dodecanoic, tridecanoic, pentadecanoic, hexadecanoic, octadecanoic, and nonadecanoic, in particular undecanoic, tridecanoic, pentadecanoic, and nonadecanoic. Carboxylic acid esters which may be advantageously used are the methyl, ethyl, and propyl esters of saturated, unbranched carboxylic acids, for example those of decanoic, undecanoic, dodecanoic, tridecanoic, pentadecanoic, hexadecanoic, octadecanoic, and nonadecanoic acids, in particular, undecanoic, tridecanoic, tetradecanoic, and nonadecanoic acids.

Of the above-mentioned aliphatic, straight-chain compounds, undecanol, nonadecanol, 1,8-diaminooctane, pentadecanoic acid, and methyl pentadecanoate, in particular pentadecanoic acid or methyl pentadecanoate, are to be singled out as being particularly desirable.

The isomers to be separated are those which are branched, in particular, those having an alkyl radical in the e-position; i.e. in the immediate vicinity of the terminal functional group of the aliphatic straight-chain compound. The alkyl radical can be a methyl, ethyl, n-propyl, i-propyl, n-butyl or i-butyl group, in particular a methyl or ethyl group, most preferably, a methyl group.

As a result of the manner of their preparation, certain reaction products contain a considerable amount of α-methyl-branched isomers. This applies particularly to those substances which are prepared by means of hydroformylation from terminal olefins and, if appropriate, are subsequently further processed. The aldehydes originating from the hydroformylation normally consist of a mixture of straight-chain unbranched aldehydes, and aldehydes which are methyl-branched in the e-position. Such aldehyde mixtures can be converted into the corresponding alcohol, carboxylic acid, and carboxylic acid ester mixtures.

A solvent and urea are added to the mixture containing the compound to be separated. An alcohol, a ketone, an ether, a hydrocarbon, and/or water can be used as the solvent. Suitable alcohols are aliphatic alcohols, in particular, aliphatic alcohols having 1 to 4 carbon atoms, preferably methanol and/or ethanol, where appropriate, as a mixture with water. Methanol is particularly usable. The use of water as the solvent, if necessary together with one or more of the above-mentioned solvents, can be helpful in numerous cases.

The choice of solvent or solvent mixture depends on the nature of the separation problem. A suitable solvent or solvent mixture should therefore be sought for the particular separation process to be carried out. The solvent or the solvent mixture should not form clathrates or adducts with urea and should also be inert towards the substances present in the solution. The use of methanol, ethanol, and/or water has proved appropriate in most cases.

The solvent and urea can be added separately and simultaneously or serially to the mixture to be separated. Usually, the solvent is added first and then the urea, with stirring. It is also possible to use the urea in the form of a solution.

The amounts of urea, based on the compound to be separated off as the clathrate, is of importance for carrying out the process according to the invention. Although a decreasing amount of urea causes an increase in the selectivity of the separation process, it also causes a reduction in yield. Conversely, an increase in the amount of urea employed leads, on the one hand, to an increase in the yield but, on the other hand, to a reduction in the selectivity of the separation process.

When specifying the amount of urea to be employed, it proves to be beneficial to take into account the chain length of the molecule in question, as well as the molar amount of compound to be separated. As a recommended value, it is advisable to use the urea in an amount such that 0.3 to 1.0, in particular 0.4 to 0.9, preferably 0.5 to 0.75, mols of urea are available per Å $(10^{-10}$ m) of the molecular chain which is to be inserted into the urea skeleton as the guest molecule. One mole of an aliphatic compound having a chain length of 12 Å thus requires 12 times the amount of the above-mentioned recommended values, calculated as moles of urea. In contrast, 0.5 mol of a compound having a chain length of, for example, 16 Å requires only 8 times the amount of the usual recommended value, calculated as moles of urea.

The chain lengths of alkanes having 7, 10, 12, and 16 carbon atoms is estimated at about 9, 13.5, 15.5, and 21 Å, respectively, and the chain length of carboxylic acids having 7, 10, 12, 16 and 18 carbon atoms is estimated at about 10, 14, 16.5, 21.5, and 24 Å, respectively. The chain lengths of carboxylic acid methyl esters and alcohols are comparable in size. A relatively precise estimation of the urea requirement can be made with the aid of these values (compare Schenck, Ann. 565, 1949, pages 204 to 240).

The process according to the invention can be carried out either batchwise or continuously. A batchwise procedure is particularly simple. The urea, or a solution containing the urea, is usually added in the desired amount to the mixture to be separated, the temperature is increased, if appropriate, while stirring, until a clear solution is obtained, and this is then cooled. It has generally proved appropriate to heat the mixture to a temperature of 25° C. to 100° C., in particular 30° C. to 90° C., preferably 35° C. to 85° C., after addition of the urea. Stirring assists in dissolving the urea.

The solution containing urea clathrates can then be cooled slowly to, for example, −25° to +50°, in particular −10° to +40°, preferably 0° to +30° C. The clathrates which have crystallized are separated, for example by decanting and/or filtering and, if appropriate, washed with cold solvent or solvent mixture.

The aliphatic, straight-chain compound, separated as the clathrate, can be liberated by dissolving the urea clathrate in water, and removing the compound from the aqueous solution, if appropriate after acidification, by extraction by means of an organic solvent. Suitable solvents include water-insoluble organic solvents, such as cyclohexane, ethyl acetate, and di-n-butyl ether, in particular ethyl acetate. If necessary, the process described above can be repeated several times.

The examples described below illustrate the invention, but do not limit it.

EXAMPLE 1

8.2 g of urea and 25 ml of a solvent mixture consisting of 8 parts by volume of isopropanol and 1 part by volume of water are added to 3.85 g of a mixture which contains 57.65% by weight of n-pentadecanoic acid and 18.12% by weight of 2-methyltetradecanoic acid. The mixture is heated, with stirring, until a clear solution is obtained.

The solution is cooled to 20° C. and the mixture is left to stand at this temperature for 24 hours. The clathrate crystals which have precipitated are then filtered off with the aid of a suction filter, and the residue on the filter is washed three times with, in each case, 10 ml of the solvent mixture, which has been cooled to 5° C.

The clathrate crystals are dissolved in water and a pH of 3 to 4 is established by addition of hydrochloric acid. The acidified aqueous solution is treated with, in each case, 20 ml of cyclohexane and extracted; this procedure is repeated twice. The resulting separate cyclohexane phases are combined, washed twice with water, and then dried over $Na_2SO_4$. After the cyclohexane is removed by evaporation, a mixture which contains 66.0% by weight of n-pentadecanoic acid, but only 2.15% by weight of 2-methyltetradecanoic acid is obtained. 60.9% by weight of the n-pentadecanoic acid employed is recovered.

In all the examples, analytic determination of the carboxylic acids is carried out, after conversion into the corresponding methyl esters, by means of gas chromatography analysis. Stearic acid is used as the internal standard.

EXAMPLE 2

72 g of urea and 180 ml of methanol are added to 24.2 g of the mixture employed in Example 1, and the mixture is heated to 60° C. with stirring until a clear solution is obtained. The solution is cooled to room temperature and the mixture is left to stand at this temperature for 24 hours. The clathrate crystals which precipitate are then filtered off with the aid of a suction filter.

About 5% by weight of the clathrate crystals obtained in this manner are taken for analytic purposes and treated as described below. The remainder is further processed as described in Example 3.

The clathrate crystals are dissolved in water. A pH of 3 to 4 is established by addition of hydrochloric acid. The acidified aqueous solution is treated with, in each case, 100 ml of ethyl acetate and extracted three times. The resulting separate ethyl acetate phases are combined, washed twice with water, and then dried over $Na_2SO_4$. After the ethyl acetate is removed by evaporation, a mixture which contains 66.1% by weight of n-pentadecanoic acid, but only 1.0% by weight of 2-methyltetradecanoic acid is obtained.

EXAMPLE 3

21 g of urea and 180 ml of methanol are added to the clathrate crystals originating from Example 2, from which a mixture containing 1.0% by weight of 2-methyltetradecanoic acid and 66.1% by weight of n-pentadecanoic acid can be isolated, and the mixture is heated at 60° C. with stirring until a clear solution is obtained. The solution is cooled to room temperature and the mixture is then left to stand at this temperature for 24 hours. The clathrate crystals which have precipitated are then filtered off with the aid of a suction filter.

The clathrate crystals are dissolved in water and further processed as described in Example 2. After addition of hydrochloric acid, extraction by means of ethyl acetate, drying of the combined organic phases, and evaporation of the ethyl acetate, a mixture which contains 76.1% by weight of n-pentadecanoic acid but only 0.22% by weight of 2-methyltetradecanoic acid is obtained.

The yield of n-pentadecanoic acid is 74.7% by weight when determined by gas chromatography and 78.9% by weight when determined by gravimetry, in each case based on the amount of n-pentadecanoic acid employed in Example 2. The yield of n-pentadecanoic acid, in each case, based on the amount of n-pentadecanoic acid employed in Example 3, is 80.1% by weight when determined by gas chromatography, and 84.6% by weight when determined by gravimetry.

EXAMPLE 4

90.3 g of a mixture which contains 52.77% by weight of methyl n-pentadecanoate and 17.71% by weight of methyl 2-methyltetradecanoate are heated in three successive stages. The amount of urea and methanol to be found in each case in the following table is added to the methyl ester mixture and the clathrate crystals resulting from stages 1 and 2, and the mixture is heated at the reflux temperature with stirring until a clear solution is obtained.

The solution is cooled to room temperature, the mixture is left to stand at this temperature for 24 hours and then cooled to +5° C. for a further 6 hours; the clathrate crystals which have precipitated are filtered off with the aid of a suction filter.

The clathrate crystals obtained in stage 3 are dissolved in water. A pH of 3 to 4 is established by addition of hydrochloric acid. The acidified aqueous solution is treated with, in each case, 100 ml of ethyl acetate and extracted three times. The resultant separate ethyl acetate phases are combined, washed twice with water, and then dried over $Na_2SO_4$. After the ethyl acetate is removed by evaporation, the mixtures identified in the following table (as determined by gas chromatography analysis) are obtained. The yield data is determined by gravimetry.

For analytical purposes, in each case, about 5% by weight of the clathrate crystals obtained in the individual stages are treated analogously to the clathrate crystals obtained in stage 3. The remaining amount of clathrates obtained from stages 1 and 2 are employed in stages 2 and 3, and further processed as specified in the preceding instructions. In the yield data, the amount diverted for analytical purposes is taken into account.

TABLE

| Stage | 1 | 2 | 3 |
| --- | --- | --- | --- |
| Urea (g) | 271 | 50 | 40 |
| Methanol (ml) | 900 | 750 | 600 |
| Starting substance (g) | 90.3 | (product from stage 1) | (product from stage 2) |
| Methyl 2-methyl-tetradecanoate (% by weight) | 6.62 | 1.75 | 0.07 |
| Methyl n-pentadecanoate (% by weight) | 66.6 | 68.5 | 67.2 |
| Yield % by weight) | 91.6 | 86.3* | 75.8* |

*Yield based on the amount of methyl n-pentadecanoate employed in stage 1

EXAMPLE 5

A mixture which contains 76.6% by weight of 1,8-diaminooctane, 0.4% by weight of 2,5-dimethyl-1,6-diaminohexane, and 12.3% by weight of 2-methyl-1,7-diaminoheptane (determined by gas chromatography) is processed in a manner analogous to that of stage 1 of Example 4. The clathrate crystals obtained are worked up in a manner analogous to that of stage 3 of Example 4. The mixture liberated from the clathrate contains, in addition to 1,8-diaminooctane as the main constituent, only 0.2 to 0.5% by weight of 2-methyl-1,7-diaminoheptane. 2,5-Dimethyl-1,6-diaminohexane is no longer present. The yield is 63% by weight, based on the 1,8-diaminooctane employed.

While only a limited number of specific embodiments of the present invention have been expressly disclosed, it is, nonetheless, to be broadly construed, and not to be limited except by the character of the claims appended hereto.

What we claim is:

1. A process for separation of an aliphatic, straight chain compound having 8 to 10 carbon atoms and a terminal functional group from an initial mixture containing isomers thereof which have branched chains at their α-positions, said process comprising addition of a solvent and urea to said initial mixture to form an aliphatic urea mixture, which then forms a urea clathrate mixture, cooling said urea clathrate mixture to crystallize out said urea clathrate, and liberating said aliphatic compound from said urea clathrate which has crystallized.

2. The process of claim 1 wherein said aliphatic urea mixture is heated to a solution temperature.

3. The process of claim 2 wherein said solution temperature is 25° C. to 100° C.

4. The process of claim 3 wherein said solution temperature is 30° C. to 90° C.

5. The process of claim 4 wherein said solution temperature is 35° C. to 85° C.

6. The process of claim 1 Wherein said straight chain has 8 to 22 carbon atoms.

7. The process of claim 6 wherein said straight chain has 10 to 19 carbon atoms.

8. The process of claim 1 wherein said terminal group is selected from the group consisting of an alcohol, amine, ether, and carboxylic acid and carboxylic acid ester radicals.

9. The process of claim 8 wherein said terminal group is selected from the class consisting of an amine, and carboxylic acid and carboxylic acid ester radicals.

10. The process of claim 9 wherein said terminal group is a carboxylic acid or carboxylic ester radical.

11. The process of claim 1 wherein said aliphatic compound is selected from the group consisting of undecanol, nonadecanol, 1,8-diaminooctane, pentadecanoic acid, and methyl pentadecanoate.

12. The process of claim 11 wherein said aliphatic compound is pentadecanoic acid or methylpentadecanoate.

13. The process of claim 1 wherein said isomers are α-alkyl branched isomers of said aliphatic compound.

14. The process of claim 13 wherein said isomers are α-methyl branched isomers.

15. The process of claim 1 wherein said solvent is selected from the group consisting of alcohols, ketones, ethers, hydrocarbons, water, and mixtures thereof.

16. The process of claim 15 wherein said alcohol is an aliphatic alcohol having 1 to 4 carbon atoms.

17. The process of claim 1 wherein urea is present in an amount of 0.3 to 1.0 mols per mol of said aliphatic compound and per Å of said straight chain.

18. The process of claim 17 wherein said amount is 0.4 to 0.9.

19. The process of claim 18 wherein said amount is 0.5 to 0.75.

20. The process of claim 1 wherein said urea clathrate mixture is slowly cooled to a crystallization temperature of −25° to 50° C.

21. The process of claim 20 wherein said crystallization temperature is −10° to 40° C.

22. The process of claim 21 wherein said crystallization temperature is 0° to 30° C.

23. The process of claim 1 wherein said urea clathrate which has been crystallized is separated from its mother liquor.

24. The process of claim 23 wherein said urea clathrate which has been separated is washed with cold said solvent.

25. The process of claim 1 wherein said aliphatic compound is liberated by dissolving said urea clathrate in water and extracting with an organic solvent.

* * * * *